United States Patent [19]

Altendorf

[11] Patent Number: 4,866,356
[45] Date of Patent: Sep. 12, 1989

[54] CIRCUIT FOR CONTROLLING THE SPEED OF A SUBFRACTIONAL HORSEPOWER DC MOTOR

[75] Inventor: Hans-Walter Altendorf, Worms, Fed. Rep. of Germany

[73] Assignee: Siemens Aktiengesellschaft, Berlin and Munich, Fed. Rep. of Germany

[21] Appl. No.: 207,786

[22] Filed: Jun. 17, 1988

[30] Foreign Application Priority Data

Jun. 25, 1987 [DE] Fed. Rep. of Germany ....... 3721032

[51] Int. Cl.⁴ .............................................. H02P 5/00
[52] U.S. Cl. .................................... 388/811; 388/817; 388/901; 388/903
[58] Field of Search ................ 318/341, 599, 331, 314

[56] References Cited

U.S. PATENT DOCUMENTS

| | | | |
|---|---|---|---|
| 3,401,324 | 9/1968 | James | 318/341 |
| 3,536,972 | 10/1970 | Lutz et al. | 318/331 |
| 3,588,654 | 6/1971 | Balazs | 318/331 |
| 4,061,950 | 12/1977 | Kayanuma | 318/314 |
| 4,454,573 | 6/1984 | Petsch et al. | 318/341 XR |
| 4,508,999 | 4/1985 | Melocik et al. | 318/331 |
| 4,510,423 | 4/1985 | Iwasawa | 318/331 |
| 4,734,630 | 3/1988 | Okano | 318/599 |

Primary Examiner—Benjamin Dobeck
Attorney, Agent, or Firm—Hill, Van Santen, Steadman & Simpson

[57] ABSTRACT

A circuit for controlling the speed of a subfractional horsepower DC motor has a driver stage with a switch that interrupts the motor current in repeated succession so that a pulse-like current is provided, and the motor EMF is sampled synchronously with the motor current interruption, with the sampled value being supplied to a comparator wherein it is compared to a rated value. The output of the comparator is used to control the driver stage which includes the switch. Two pulse duration modulators are provided which respectively independently control the motor current and voltage. The pulse duration modulator which controls the current generates pulse pauses which are always sufficiently long to permit the EMF measurement to be completed. The pulse duration modulator operates at a frequency above the audible frequency range so that its pulse pauses are short enough to prevent the motor current from noticeably failing or being completely interrupted.

12 Claims, 2 Drawing Sheets

CIRCUIT FOR CONTROLLING THE SPEED OF A SUBFRACTIONAL HORSEPOWER DC MOTOR

BACKGROUND OF THE INVENTION

1. Field of the Invention

The present invention is directed to electronic circuitry for controlling the speed of a subfractional horsepower DC motor having a switch which repeatedly interrupts the motor current to generate a pulse-like current, with the motor EMF being monitored synchronously with the interruption of the motor current, i.e., after each interruption, with the sensed value being supplied to a comparator, with the output of the comparator being used to control a driver stage which includes the switch.

2. Description of the Prior Art

Subfractional horsepower DC motors ar used for driving small tools such as dental instruments, such as drills, grinders and the like. These motors operate in a voltage range of up to 24 volts. To permit such tools to operate within a large speed range (between a few hundred and 160,000 rpm), the motor must be similarly adjustable in speed over a wide range. In a known subfractional horsepower DC motor of this type, it is possible to vary the speed between about 2,000 and 40,000 rpm. Different gearing reductions and increases can be used to further decrease the minimum speed, or further increase the maximum speed, at the point of attachment of a tool. Such gearing can be attached to the drive shaft of the motor or at the head of a handpiece which accepts the tools.

German OS No. 32 21 146 discloses a circuit of the type described above wherein the speed is controlled by clocking the operating voltage and undertaking an EMF measurement during the pauses between the pulses. An interrupt circuit is provided in the motor drive circuit for this purpose. A sample and hold circuit samples and stores the motor voltage, and a regulator is provided which is supplied with a rated value and the actual value of the motor voltage from the sample and hold circuit. A timing circuit is also provided which activates the interrupt circuit to repeatedly briefly interrupt the motor current, and which also activates the sample and hold circuit to cause the value of the motor voltage to be sampled with a slight delay following the beginning of the interruption of the motor current, but before resumption of the motor current, i.e., before resumption of the leading edge of the next current pulse.

In this known circuit, the motor is operated as a generator in the interrupt phase, and the EMF of the motor-acting-as-generator is used as the actual value for the control circuit. Interruption of the motor power supply is timed to begin after the field dismantling phase. In this known circuit, the sampling frequency or repetition rate is between 10 and 1,000 Hz, and the sampling time is between 5 and 30 microseconds given a turn-off time of the motor current of from 250 through 500 microseconds. This known circuit is comparatively complex, particularly because a controllable voltage source must be provided, with a relatively expensive power stage, which must be designed to accommodate substantially the entire operating power.

SUMMARY OF THE INVENTION

It is an object of the present invention to provide an electronic control circuit for a subfractional DC motor which is simplified, and thus less expensive, in comparison to known motor control circuits.

The above object is achieved in accordance with the principles of the present invention in a control circuit which processes the full, unregulated operating voltage without the necessity of a switching regulator, or the generation of a stabilized voltage source for generating the motor voltage. A particularly vibration-free operation of the motor can also be achieved in accordance with the principles of the present invention by undertaking a correspondingly high sampling frequency of one pulse duration modulator and using this frequency to modulate the output of another lower frequency pulse duration modulator.

DESCRIPTION OF THE PREFERRED EMBODIMENTS

Figure 1:
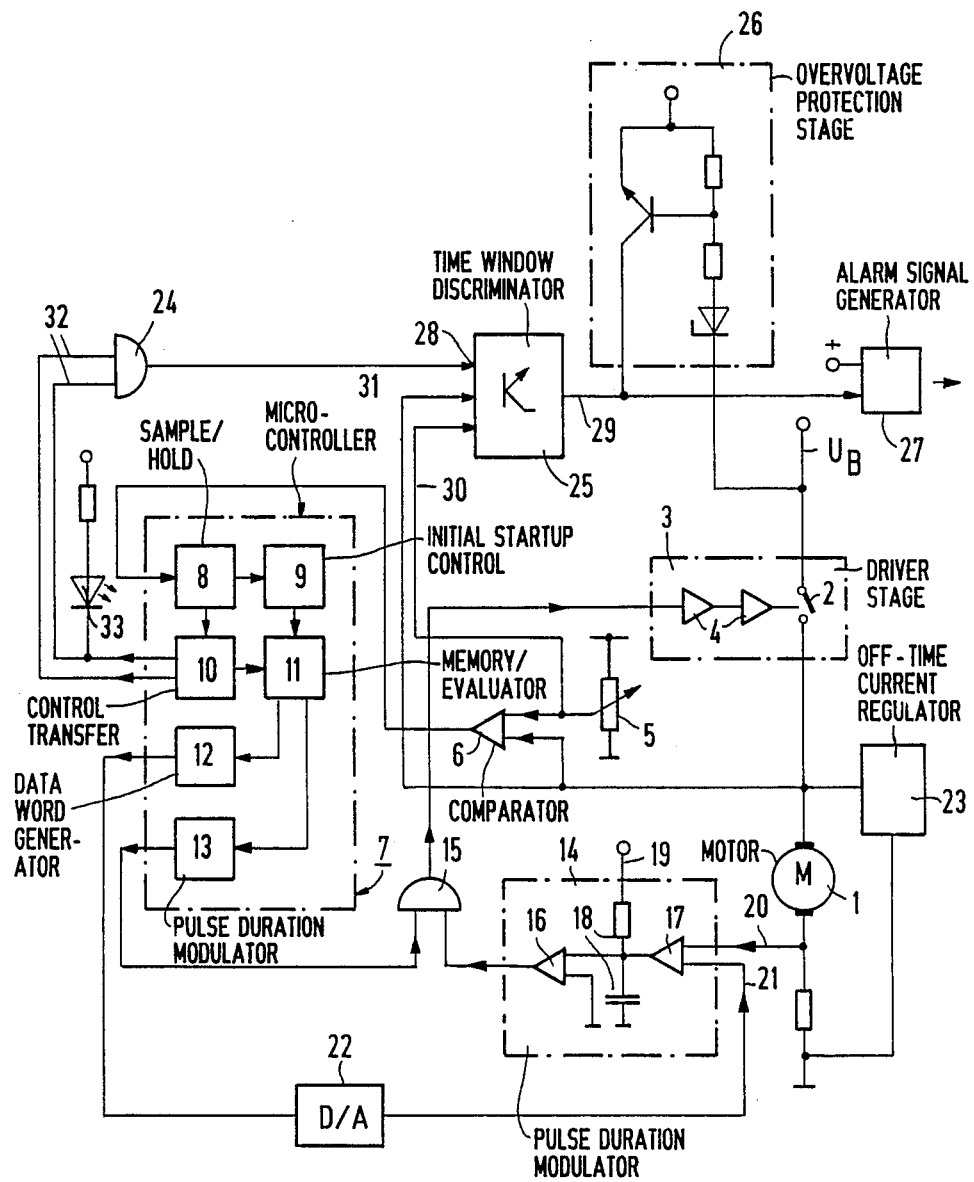
FIG. 1 a block circuit diagram of a circuit for controlling the speed of a subfractional horsepower DC motor constructed in accordance with the principles of the present invention.

A circuit as shown in FIG. 1 constructed in accordance with the principles of the present invention for controlling the speed of a subfractional horsepower DC motor of the type suitable for use in driving dental equipment. As shown in FIG. 1, a motor 1 is supplied with a voltage $U_B$, and a current, from an input terminal. An interrupter 2 is connected between the terminal and the motor 1, the interrupter 2 being a component in a driver stage 3. The driver stage 3 includes at least one driver (amplifier) 4, and preferably contains two such drivers. The rated speed of the motor 1 can be set in a known manner with an actuator (potentiometer) 5. The actual value of the motor speed is taken directly from the motor circuit, and is supplied, with the output of the actuator 5, to a comparator 6. The output of the comparator 6 does not include a determination of repetitive error, but only provides yes/no information as to whether the actual motor speed value is higher or lower than the rated value. This information is forwarded to a microcontroller referenced 7.

In the microcontroller 7, the output of the comparator 6 is supplied to a sample/hold stage 8 which samples the output of the comparator 6 at the appropriate point in time, and stores this value until the next sampling. The proper point in time for the sampling is immediately after the dismantling of the magnetic field which is generated by the motor winding. In the intervening time, the information at the output of the comparator 6 has no value, and is not used by the sample/hold stage 8. Sampling of the output of the comparator 6 at the proper point in time supplies the sample/hold stage 8 with information as to whether the motor EMF at the time of sampling is higher or lower than the actual value which has been set. The sample/hold stage 8 supplies outputs to an initial start-up control stage 9 and to a control transfer stage 10. The initial start-up control stage 9 controls the operation of the motor 1 during the initial part of start-up, until usable information is present in the sample/hold stage 8. For this purpose, the initial start-up control stage 9 enters data in a memory/evaluator 11. The outputs of the memory/evaluator 11, based on the inputs from the initial start-up control stage 9, are used to operate the motor 1 via the components respectively connected to the outputs of the memory/evaluator 11, as described in further detail below.

The control transfer stage 10 determines when sufficient useful data has been obtained from the sample/hold stage 8 to transfer control of the motor 1 from the initial start-up control stage 9. Any number of different criteria can be used by the control transfer stage 10 to determine when transfer of control is to occur, at which point the initial start-up control stage 9 becomes disconnected from the circuit and the control transfer stage 10 takes over control of the motor 1 via the memory/evaluator 11.

Figure 2:
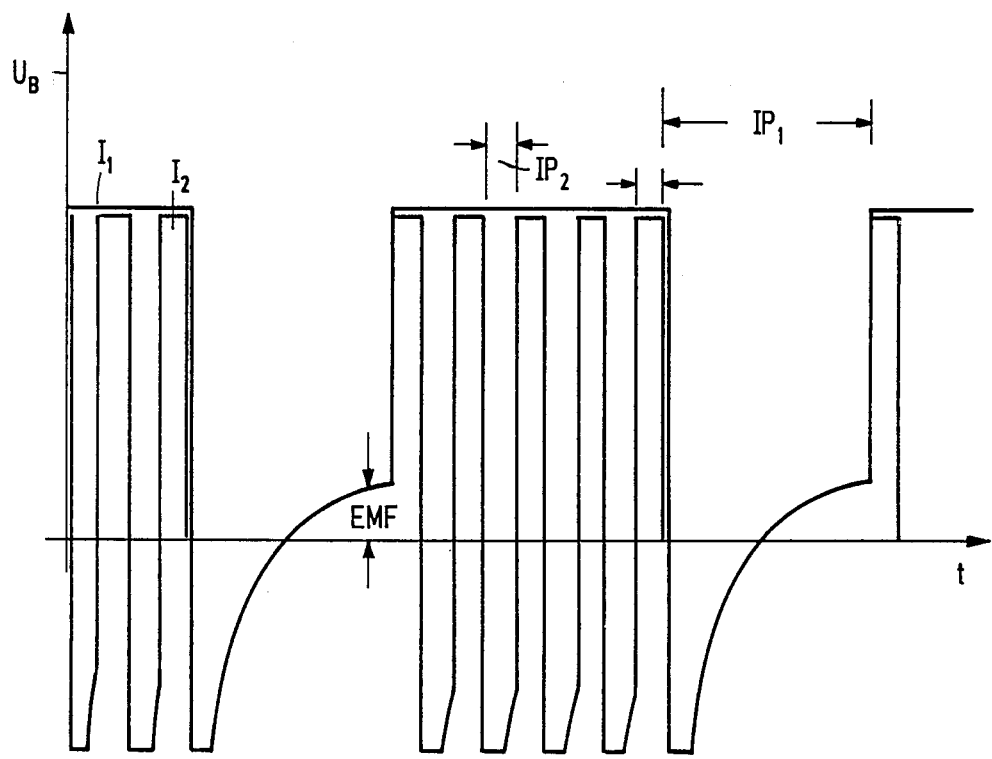
FIG. 2 is a voltage/time diagram for explaining the operation of the circuit of FIG. 1.

The memory/evaluator 11 consists of a memory in which information concerning the starting condition and the energy supply to the motor are entered and updated. Using this data, a first pulse duration modulator 13 is driven, which generates low-frequency pulses $I_1$ (see FIG. 2) of about 10 Hz through about 10 kHz, the amplitudes of the pulses $I_1$ changing with the operating voltage $U_B$ of the motor 1. As shown in FIG. 2, the pauses $IP_1$ between the pulses $I_1$ of the first pulse duration modulator 13 are sufficiently long to permit an EMF measurement to be undertaken.

Data from the memory/evaluator 11 are also supplied to a data word generator 12, which generates a binary data word which is supplied to a digital-to-analog converter 22. The output of the converter 22 is supplied as one input of a second pulse duration modulator 14. Dependent upon the data in the memory/evaluator 11, entered therein via stages 9 and 10, the data word generator 12 generates either parallel or serial data words, which result in a voltage at line 21 indicating how high the motor current should become during a pulse in the pulse duration modulator 14.

The pulse duration modulator 14 includes two comparators 16 and 17 and an RC element 18 having a terminal 19 at which a stable voltage is present. As shown in FIG. 2, the pulse duration modulator 14 generates pulses $I_2$ at a higher frequency than the pulses $I_1$, and has pauses $IP_2$ between the pulses $I_2$ which are small enough to prevent the motor current, which is supplied to the modulator 14 on line 20, from dropping too far, or from being completely interrupted. Preferably, the motor current should not drop farther than about 10% below the average motor current. As noted above, the frequency of the output of the pulse duration modulator 14 is much higher than that of the pulse duration modulator 13, and preferably is above the audible frequency range, i.e., greater than 20 kHz. The comparator 17 compares the voltage dependent on the motor current taken from line 20 to the voltage on line 21 supplied from the converter 22. The output of the comparator 17 discharges the capacitor of the RC element 18, which determines the off-time (pulse pause $IP_2$) of the pulse duration modulation.

The pulse duration modulator 13, as noted above, generates a pulse duration modulated signal having pauses between the pulses permitting interpretable information to be generated by the comparator 6 and the sample/hold circuit 8. The modulator 13 is not identical to the modulator 14, the modulator 13 being capable of processing considerably more control parameters than the modulator 14, but the modulator 13 processes those parameters relatively slowly, which is why the additional modulator 14 is needed.

The outputs of the modulators 13 and 14 are combined in an AND gate 15, the output of which is supplied to the driver stage 3. The signal supplied from the gate 15 causes the interrupter 2, and thus the motor circuit, to be closed only during the presence of output pulses from both modulators 13 and 14. One advantage of this circuit is that only a single power stage is required. Filtering can also be eliminated, because the motor can be directly operated with the modulated voltage. The overall executive sequencing, including the time-monitoring with respect to the EMF rise and the low-frequency pulse duration modulation is undertaken by the microcontroller 7.

The cut-in time is determined by the complex load of the motor 1. The inductance of the motor generates a linear current rise, given a voltage discontinuity, and the linear current rise is used for generating the cut-in time dependent on the voltage at the motor and the inductance of the motor. Because the voltage/time integral $\int u(t)dt$, which effectively lies above the inductance of the motor during a pulse, is maintained constant by the regulation (the ohmic part of the motor load being compensated by the regulation) and the inductance of the motor is constant, the cut-in time also remains approximately constant given a load on the motor, insofar as the control voltage received on the line 21 does not change.

The digital-to-analog converter 22 is of a type which permits the switching threshold of the comparator 17 to be varied, this being equivalent to a variation of the peak current through the motor 1. As a result, the off-time of the motor remains constant, and the cut-in time is lengthened, so that the effective current through the motor becomes greater. As mentioned above, the off-time is selected so short that the motor current drops by only about 10% during this time. During this time span, the motor 1 is supplied with current through an off-time current regulator 23, which also functions to divert inductive voltage peaks occurring at the clock edge.

The digital-to-analog converter 22 may be one of several known types. The converter 22 may convert an arbitrary binary code into a voltage or a current, may be a frequency/voltage converter which converts a frequency prescribed by the output of the microcontroller 7 into a voltage or into a current, may be a filter element which forms the mean value from a pulsed voltage output from the microcontroller 7, or may be a time-/voltage converter which converts a time difference between two pulses from the microcontroller 7 into a voltage or into a current. The converter 22 may include a sample/hold amplifier following the converting circuitry, or a saw tooth generator with a peak value detector.

For cost reasons, the converter 22 may alternatively be a resistor network, which has the advantage that no active components are required for the converter 22, since the input of the comparator 17 will already exhibit high impedance, given the use of standard components.

The control transfer stage 10 also generates a binary signal which controls a light emitting diode 33. The light emitting diode 33 permits the functioning of the microcontroller 17 to be visually ascertained. When the motor 1 is at a standstill, i.e., is shut off, the microcontroller 7 can undertake a self-test. The light emitting diode 33 flashes when no fault is present; when a fault is present, the light emitting diode 33 will not be illuminated, or may constantly be illuminated. When the motor 1 is in operation, the energy output to the motor 1 can be visually estimated on the basis of the brightness of the light emitting diode 33, i.e., if the light emitting diode is brightly illuminated, the motor is requiring little power; when high power is being required by the motor 1, the light emitting diode 33 will not be illuminated as brightly. The transition from low to high illumination can be infinitely variable. Although the light emitting diode 33 is supplied with a binary signal from the control transfer stage 10, and thus is actually flashing under all conditions, the human eye will integrate the flashing signal, and thus an observer will have the impression of an analog change in brightness.

The circuit also includes a time window discriminator 25. The time window discriminator 25 is supplied on line 30 with the rated value from the actuator 5, and with the actual value for the motor 1 on line 31. The time window discriminator 25 is inhibited by a signal on line 28 from a gate 24 except during the pulse pause time $IP_1$. This is achieved by signals on lines 32 from the control transfer stage 10 supplied to the gate 24. Doubling of these signals is provided for safety reasons, otherwise a direct output could simply be taken from the control transfer stage 10 to the inhibit input of the time window discriminator 25.

The time window discriminator 25 compares the actual value obtained at the final control element (i.e., the output of the driver stage 3) to the rated value and generates a signal on line 29 if the result of the comparison shows the actual value to impermissibly deviate from the rated value. In the event such impermissible deviation occurs, an alarm signal is generated by an alarm signal generator 27, and a transistor in an overvoltage protection stage 26 becomes conducting, so that the volta $U_B$ is across the overvoltage protection stage 26, instead of the motor 1. By using two signals on lines 32, combined in gate 24 to generate an inhibit signal on line 28, it is insured that even if a small chronological offset exists with respect to the pulse pause $IP_1$, this will not cause the comparison in the time window discriminator 25 to be undertaken at an incorrect time, thereby generating a false alarm signal. By inhibiting the time window discriminator 25 in this manner, it is insured that the rated value will not be erroneously compared to the operating voltage $U_B$, or the negative shut-off spike of the motor inductance, both of which would erroneously trigger an alarm signal because the rated value is never permitted to reach the value $U_B$, and definitely cannot be negative.

Although modifications and changes may be suggested by those skilled in the art it is the intention of the inventor to embody within the patent warranted hereon all changes and modifications as reasonably and properly come within the scope of his contribution to the art.

I claim as my invention:

1. A circuit for controlling the speed of a subfractional horsepower DC motor comprising:
    means for pulse-like interrupting current to said motor;
    means for sampling the EMF of said motor following each current interruption to obtain a sampled EMF value corresponding to motor speed;
    means for comparing said sampled EMF value to a rated
    EMF value to obtain a comparison result; first pulse duration modulator means for generating a first pulse train based on said comparison result, said first pulse train having pauses between pulses of a duration permitting sampling of said EMF by said means for sampling to be completed;
    second pulse duration modulator means for generating a second pulse train based on said comparison result, said second pulse train having pauses between pulses of a duration preventing said motor current from decreasing substantially during said second pulse train pauses; and
    means for combining said first and second pulse trains to generate a control signal for said means for interrupting setting the duration of interruption of said current.

2. A circuit as claimed in claim 1, wherein said means for combining is an AND gate.

3. A circuit as claimed in claim 1, wherein said second pulse duration modulator means comprises;
    a first comparator having a first input supplied with a voltage corresponding to said motor current and a second input supplied with a signal based on said comparison result;
    an RC element connected to the output of said first comparator so that said output of said first comparator discharges a capacitor in said RC element to set said duration of said pauses of said second pulse train; and
    a second comparator having a first input connected across said capacitor of said RC element and having a second input supplied with a fixed value, and having an output connected to said means for combining.

4. A circuit as claimed in claim 1, further comprising a microcontroller having an input supplied with said comparison result, said first pulse duration modulator means being a part of said microcontroller.

5. A circuit as claimed in claim 4, wherein said microcontroller, in addition to said first pulse duration modulator means, comprises:
    sample/hold means for repeatedly sampling said comparison result and holding the sampled value until a next sampling;
    initial motor start-up control means supplied with the repeatedly sampled and held values from said sample/hold means for controlling operation of said motor for an initial period of time following start-up of said motor;
    control transfer means also supplied with said repeatedly sampled and held values from said sample/hold means for transferring control of said motor from said initial start-up control means after said initial period based on said sampled and held values;
    memory means supplied with outputs from said initial start-up control means and said control transfer means for supplying signals to said first and second pulse duration modulator means based on signals from said initial start-up control means during said initial period and based on said sampled and held values thereafter; and
    data word generator means connected between an output of said memory means and said second pulse duration modulator means.

6. A circuit as claimed in claim 4, further comprising a digital-to-analog converter connected between an output of said microcontroller and said second pulse duration modulator means.

7. A circuit as claimed in claim 4, further comprising a resistor network connected between an output of said microcontroller and said second pulse duration modulator means.

8. A circuit as claimed in claim 4, further comprising:

monitoring means for determining whether said motor EMF is within a selected window; and means in said microcontroller for generating an inhibition signal for said means for monitoring so that said means for monitoring monitors said EMF only at selected times correlated with said control signal from said means for combining.

9. A circuit as claimed in claim 8, wherein said means for monitoring has a first input supplied with the motor voltage and a second input defining a middle of said window supplied with said rated EMF value.

10. A circuit as claimed in claim 8, further comprising:

an overvoltage protection means connected to an output of said means for monitoring for diverting the operating voltage from said motor if an upper limit of said window is exceeded.

11. A circuit as claimed in claim 10, further comprising means connected to said overvoltage protection means for generating an alarm signal when said upper limit of said window is exceeded.

12. A circuit as claimed in claim 4, further comprising a light emitting diode, and means in said microcontroller for generating a test signal supplied to said light emitting diode indicating the functioning of said microcontroller.

* * * * *